(12) United States Patent
Bueno et al.

(10) Patent No.: US 9,186,048 B2
(45) Date of Patent: Nov. 17, 2015

(54) HERMETICALLY SEALED BOROSCOPE PROBE TIP

(71) Applicant: General Electric Company, Schenectady, NY (US)

(72) Inventors: Manuel Kenneth Bueno, Syracuse, NY (US); Eugene Carl Schiefer, Liverpool, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 153 days.

(21) Appl. No.: 13/856,470

(22) Filed: Apr. 4, 2013

(65) Prior Publication Data

US 2014/0301705 A1 Oct. 9, 2014

(51) Int. Cl.
*G02B 6/32* (2006.01)
*A61B 1/00* (2006.01)
*G02B 7/02* (2006.01)
*G02B 23/24* (2006.01)
*G01N 21/954* (2006.01)

(52) U.S. Cl.
CPC .......... *A61B 1/00167* (2013.01); *A61B 1/00096* (2013.01); *G02B 7/02* (2013.01); *G02B 23/2476* (2013.01); *G01N 21/954* (2013.01); *Y10T 29/49826* (2015.01)

(58) Field of Classification Search
None
See application file for complete search history.

(56) References Cited

U.S. PATENT DOCUMENTS

| 4,222,629 | A | * | 9/1980 | Dassele et al. | 385/94 |
| 4,238,704 | A | * | 12/1980 | Bonk et al. | 313/113 |
| 5,500,917 | A | * | 3/1996 | Daniel et al. | 385/99 |
| 6,122,430 | A | | 9/2000 | Bookbinder et al. | |
| 7,146,075 | B2 | * | 12/2006 | Tinch et al. | 385/33 |
| 8,063,560 | B2 | | 11/2011 | Aitken et al. | |
| 2003/0066311 | A1 | * | 4/2003 | Li et al. | 65/43 |
| 2005/0012053 | A1 | * | 1/2005 | O'Leary et al. | 250/504 R |
| 2005/0123240 | A1 | * | 6/2005 | Seto et al. | 385/35 |
| 2014/0058201 | A1 | * | 2/2014 | Mizuyoshi | 600/129 |

* cited by examiner

*Primary Examiner* — Mike Stahl
(74) *Attorney, Agent, or Firm* — Cooper Legal Group, LLC

(57) ABSTRACT

An optical system for inspecting an area includes an optical housing and an optical element housed within the optical housing. The optical housing houses one or more optical fibers. The optical element housed within the optical housing focuses light onto the one or more optical fibers. A sealing member seals the optical element with respect to the optical housing. The sealing member includes a solidified glass frit material. In one example, the sealing member is disposed annularly between the optical housing and the optical element. A method of forming the optical system is also provided.

20 Claims, 5 Drawing Sheets

HERMETICALLY SEALED BOROSCOPE PROBE TIP

BACKGROUND OF THE INVENTION

1. Field of the Invention

The present invention relates generally to boroscope assemblies, and more particularly, to sealing an optical element within a boroscope assembly.

2. Discussion of the Prior Art

Boroscopes are known and used in many different applications. Boroscopes are used, for example, to inspect an area by acquiring images of the area. Boroscopes commonly include boroscope probe tips for housing optical elements (e.g., lenses, fiber optic bundles, etc.) associated with the acquiring of images. In the past, a polyepoxide material (e.g., epoxy) was used to seal the optical elements and limit the passage of condensation, moisture, etc. into an interior of the boroscope probe tips.

However, the boroscope probe tips are used in areas that have relatively high temperature fluctuations. Further, depending on the particular area, the boroscope probe tips are exposed to relatively corrosive chemicals. This temperature fluctuation and/or chemical exposure is detrimental and corrosive to the seal, thus allowing for condensation, moisture, etc. to enter the boroscope probe tips.

Accordingly, it would be beneficial to seal optical elements within boroscope probe tips that withstand temperature fluctuations and chemical attacks.

BRIEF DESCRIPTION OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect, an optical system for inspecting an area is provided. The optical system includes an optical housing configured to house one or more optical fibers. An optical element housed within the optical housing focuses light onto the one or more optical fibers. A sealing member seals the optical element with respect to the optical housing. The sealing member includes a solidified glass frit material.

In accordance with another aspect, an optical system for inspecting an area is provided. The optical system includes an optical housing that is configured to house one or more optical fibers. An optical element housed within the optical housing focuses light onto the one or more optical fibers. A sealing member is disposed annularly between the optical housing and the optical element. The sealing member includes a solidified glass frit material forming a seal with the optical housing and the optical element.

In accordance with another aspect, a method of forming an optical system is provided. The method includes the steps of providing an optical housing and providing an optical element. The method further includes the step of depositing a sealing member on at least one of the optical housing and the optical element, the sealing member including a glass frit material. The method includes the step of heating the sealing member to hermetically seal the optical element to the optical housing.

BRIEF DESCRIPTION OF THE DRAWINGS

The foregoing and other aspects of the present invention will become apparent to those skilled in the art to which the present invention relates upon reading the following description with reference to the accompanying drawings, in which.

DETAILED DESCRIPTION OF THE INVENTION

Figure 1:
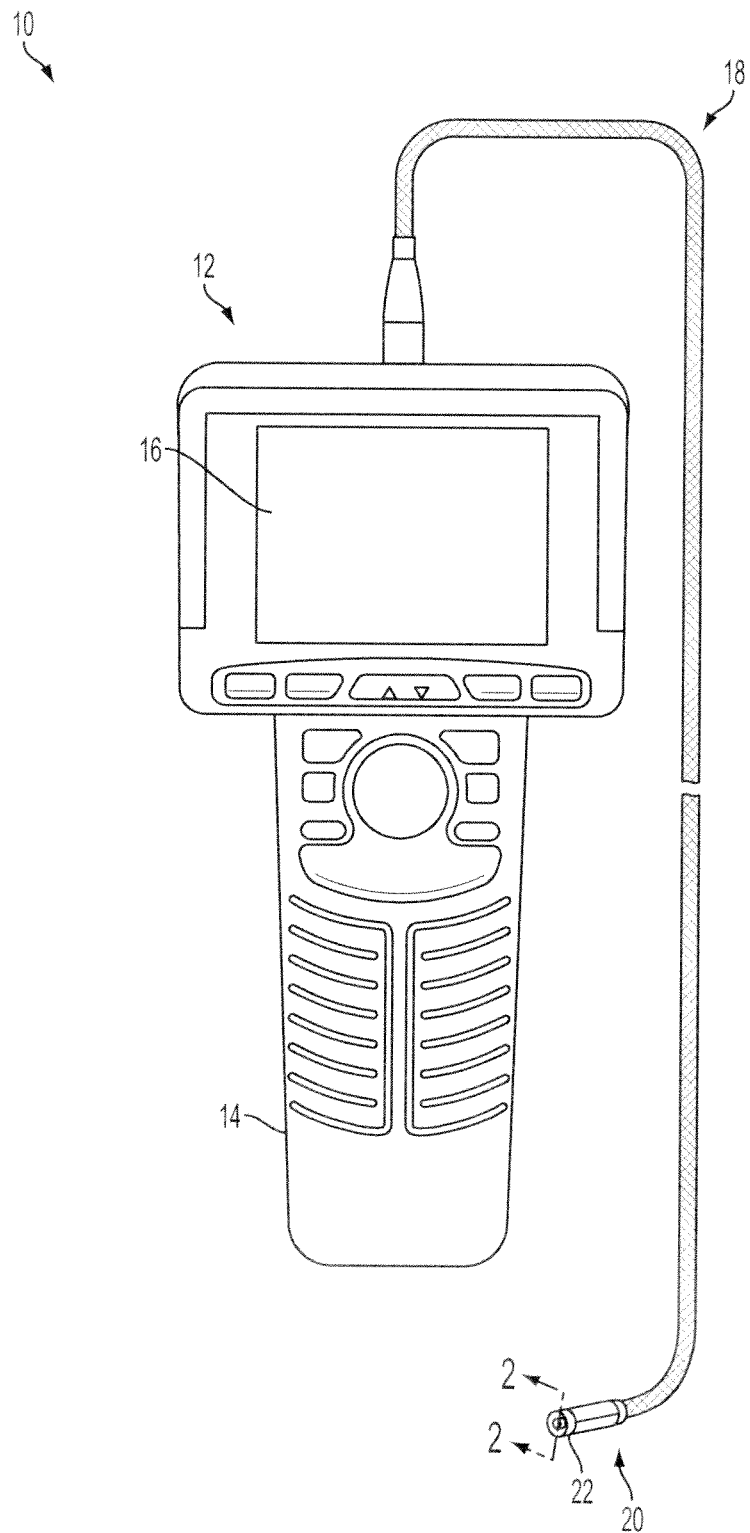
FIG. 1 illustrates an example optical system including an example camera assembly in accordance with one aspect of the invention.

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

FIG. 1 illustrates an example optical system 10 in accordance with an aspect of the invention. In general, the optical system 10 is used to monitor and/or inspect an area. The optical system 10 is somewhat generically/schematically depicted in FIG. 1, as the optical system 10 includes any number of constructions and configurations. In general, the optical system 10 will monitor, inspect, etc. an area by acquiring (e.g., capturing, recording, etc.) images/video. The optical system 10 can include any number of devices, such as a boroscope assembly, video probes, fiberscopes, cameras, etc. FIG. 1 depicts the optical system 10 as including the boroscope assembly, however, the optical system 10 is not limited to this structure, and could include other structures associated with the aforementioned devices.

The optical system 10 includes a number of structures associated with acquiring images/video. The optical system 10 includes, for example, a control apparatus 12. The control apparatus 12 is somewhat generically/schematically shown. In the shown example, the control apparatus 12 includes a handle portion 14. The handle portion 14 is sized and shaped to be grasped by a human hand. The handle portion 14 can include one or more control/function buttons that allow a user to control and/or input information to the control apparatus 12. The control/function associated with the buttons may be varied and need not be a specific limitation upon the present invention. Further, the handle portion 14 is not limited to the structure in the shown example, and can take on a number of configurations and structures.

The control apparatus 12 further includes a display screen 16. Within the shown example, the display screen 16 is located above the handle portion 14. The control apparatus 12 can include video controllers, drivers, etc. to provide imagery upon the display screen 16. The display screen 16 can display images/video of the area. It is to be understood that the display screen 16 is not limited to being located within the control apparatus 12, and in further examples, the display screen 16 may be located within a separate structure from the control apparatus 12. It is to be appreciated that the undesired presence of moisture/condensation within portions of the optical system 10 may adversely affect the display of images/video on the display screen 16.

The optical system 10 further includes a probe assembly 18. The probe assembly 18 is attached at one end to the control apparatus 12. In one example, the probe assembly 18 is an elongated, flexible structure, in which a portion of the probe assembly 18 can be moved and/or articulated. It is to be appreciated that the probe assembly 18 shown and described herein is only one example of a variety of different examples of the probe assembly 18. The probe assembly 18 can house wires, articulation cables, fiber optic bundles, etc. while providing protection to the wires from scratches, tears, environmental effects, or the like. By being elongated, the probe assembly 18 can be inserted into areas that have some limitation concerning physical/visual accessibility.

The optical system 10 further includes a camera assembly 20 disposed at an end of the probe assembly 18. In particular, the camera assembly 20 is positioned at the end of the probe assembly 18 that is opposite the control apparatus 12. In the shown example, the camera assembly 20 includes a boroscope probe tip that includes the aforementioned optical element(s) 24. The camera assembly 20 can include any number of image acquiring devices for capturing/storing images and/or video of the area. The camera assembly 20 can be positioned within the area, with the camera assembly 20 operating to acquire images of the area.

Figure 2:
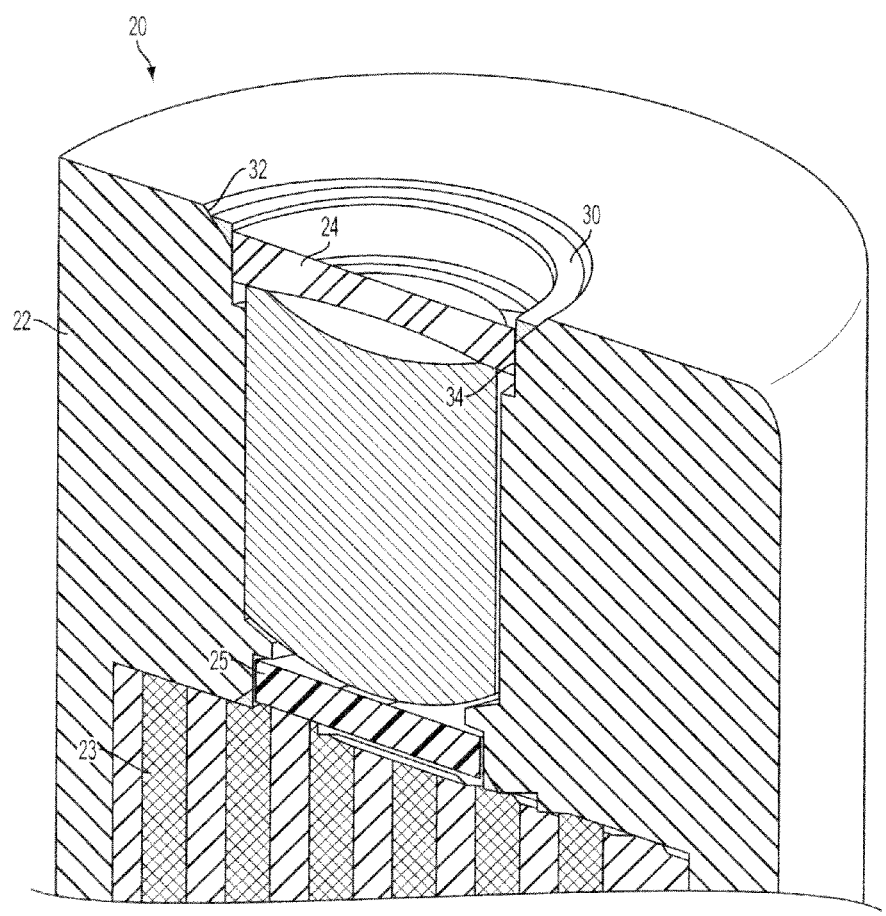
FIG. 2 is a sectional view along line 2-2 of FIG. 1 showing a cross-section of the camera assembly.

Turning now to FIG. 2, a sectional view of a camera assembly 20 and associated optical element(s) 24 are shown. It is to be appreciated that only a generic, schematic cross-section of the camera assembly 20 and optical element(s) 24 is depicted in this example for illustrative purposes and to more clearly show certain aspects of the interior of the camera assembly 20. Further, in operation, the camera assembly 20 will be fully assembled in a manner similar to that shown in FIG. 1.

The optical system 10, at the camera assembly 20, includes the optical housing 22. The optical housing 22 can be of any number of structures that can house the optical element(s) 24 (e.g., one or more lenses, apertures, filters, fiber optics, etc.). The optical housing 22 can be included as part of the probe assembly 18 or, in other examples, can be operatively attached to the probe assembly 18. In particular, the optical housing 22 is attached to the end of the probe assembly 18. The optical housing 22 can include metallic materials (e.g., stainless steel, etc.), though in other examples, the optical housing 22 may only be partially formed of metal or may be formed by non-metallic materials.

The optical housing 22 can receive a number of different structures related to image acquiring, such as optical fibers 23 (e.g., fiber optic bundles, cables, wires, or the like). It is to be appreciated that the optical fibers 23 (e.g., fiber optic bundles, cables, wires or the like) housed in the optical housing 22 are depicted somewhat generically/schematically in FIG. 2, as the optical fibers 23 (e.g., fiber optic bundles, cables, wires, or the like) include any number of sizes, shapes, and constructions. However, in operation, the optical fibers 23 (e.g., fiber optic bundles, cables, wires, or the like) can extend at least partially through an interior of the optical housing 22. The optical housing 22 will protect the optical fibers 23 from environmental conditions including moisture, humidity, condensation, high/low temperatures, etc. The optical fibers 23 can assist in transmitting light from the optical housing 22 to the control apparatus 12.

As mentioned, the optical housing 22 houses the optical element(s) 24. In addition, as mentioned, the optical element(s) 24 can be one or more element, and can includes lenses, apertures, filters or the like. The example shown within FIG. 2 includes three optical elements, but other examples could include more than or less the three shown optical elements. The optical elements 24 assist in the acquiring of images from the area. In one example, the optical elements 24 will function to focus light from the area, such as onto the optical fibers 23 (e.g., fiber optic bundles, or the like). The optical element(s) 24 can include, for example, concave lenses, convex lenses, or the like. Herein, the one or more optical elements 24, regardless of number and type/construction is/are referred to simply as the optical element 24.

In addition to the optical element(s) 24, the optical housing 22 can further house a second optical element 25. The second optical element 25 can be positioned adjacent the optical fibers 23 within the optical housing 22. The second optical element 25 can include any type of lens, such as a concave lens, convex lens, or the like. Likewise, the second optical element 25 can be larger or smaller in size than as shown. The second optical element 25 can function by further focusing/directing light from the area onto the optical fibers 23.

The optical system 10, at the camera assembly 20, further includes a sealing member 30 for sealing the optical element 24 with respect to the optical housing 22 so as to limit the passage of moisture and/or condensation into the optical housing 22. In one example, the sealing member 30 will seal the optical element 24 directly to the optical housing 22. In another example, the sealing member 30 can indirectly seal the optical element 24 and the optical housing 22, such as by including an intermediate layer between the optical element 24 and the optical housing 22. It is to be appreciated that if there are plural optical elements 24, the sealing member 30 may seal only one optical element 24 or only a portion of the plural optical elements 24. For example, an outermost one of plural optical elements 24 may be sealed. It is to be appreciated that such sealing of one or less than all of a plurality of optical elements 24 is to be considered to be a sealing of the optical elements 24 as a collective whole. In addition, it is to be recalled that plural optical elements 24 are to be considered to be included within a general descriptive term of "optical element" and thus sealing of one or some of the plurality is to be considered as a sealing of the descriptive term "optical element."

The sealing member 30 includes a frit material. In one example, the sealing member 30 includes a glass frit material. The frit material is initially in particulate/powder form. Further, in one example, the sealing member 30 includes a solidified frit material (e.g., solidified glass frit material). In yet another example, the sealing member 30, including the glass frit material, will initially be in a powder form. This powderized glass frit material includes, for example, silicate glass, pastes containing glass powder, organic binder materials, (in)organic fillers, solvents, etc. The powderized glass frit material includes a variety of glass frit powder sizes, such as by being in the range of micron-level sized particles.

The frit that provides the sealing member 30 is heatable to achieve a fluid or semifluid state so that the frit particles can flow together. After heating the powder, the sealing member 30 will form the solidified glass frit material. Some of the material included in the powderized glass frit may be burned off during the heating process, including the organic binder materials, etc. The sealing member 30 will seal, such as at a hermetically seal level, the optical housing 22 to the optical element 24. By forming a hermetic seal, the sealing member 30 is generally airtight and resistant to the passage of water, moisture, condensation, etc. through the sealing member 30.

As shown in FIG. 2, the sealing member 30 can be positioned adjacent and in contact with the optical housing 22 and optical element 24 in a variety of locations/configurations. In the shown example, the sealing member 30 is disposed in an annular groove 32 formed in the optical housing 22. The annular groove 32 has a generally shape that matches a shape of an outer edge of the optical element 24 (e.g., circular shape in the shown example). Of course, the groove 32 is not limited to including the annular/circular shape, and can include any number of sizes and shapes, including shapes that may or may not match the shape of the optical element 24. The groove 32 is bound on one side (e.g., an outer side) and open on an opposing side to the optical element 24. The sealing member 30 is disposed at least partially within the groove 32 initially, such that the frit providing the sealing member 30 will flow when heated and substantially surround/contact the optical element 24.

It is to be understood that in other examples, the optical housing 22 is not limited to including the groove 32. Rather, the optical housing 22 may not include the groove 32, and instead, the sealing member 30 will be deposited directly onto one or both of the optical housing 22 and optical element 24. Accordingly, the example shown in FIG. 2 includes only one example arrangement of the optical housing 22, optical element 24, and sealing member 30.

Figure 3:
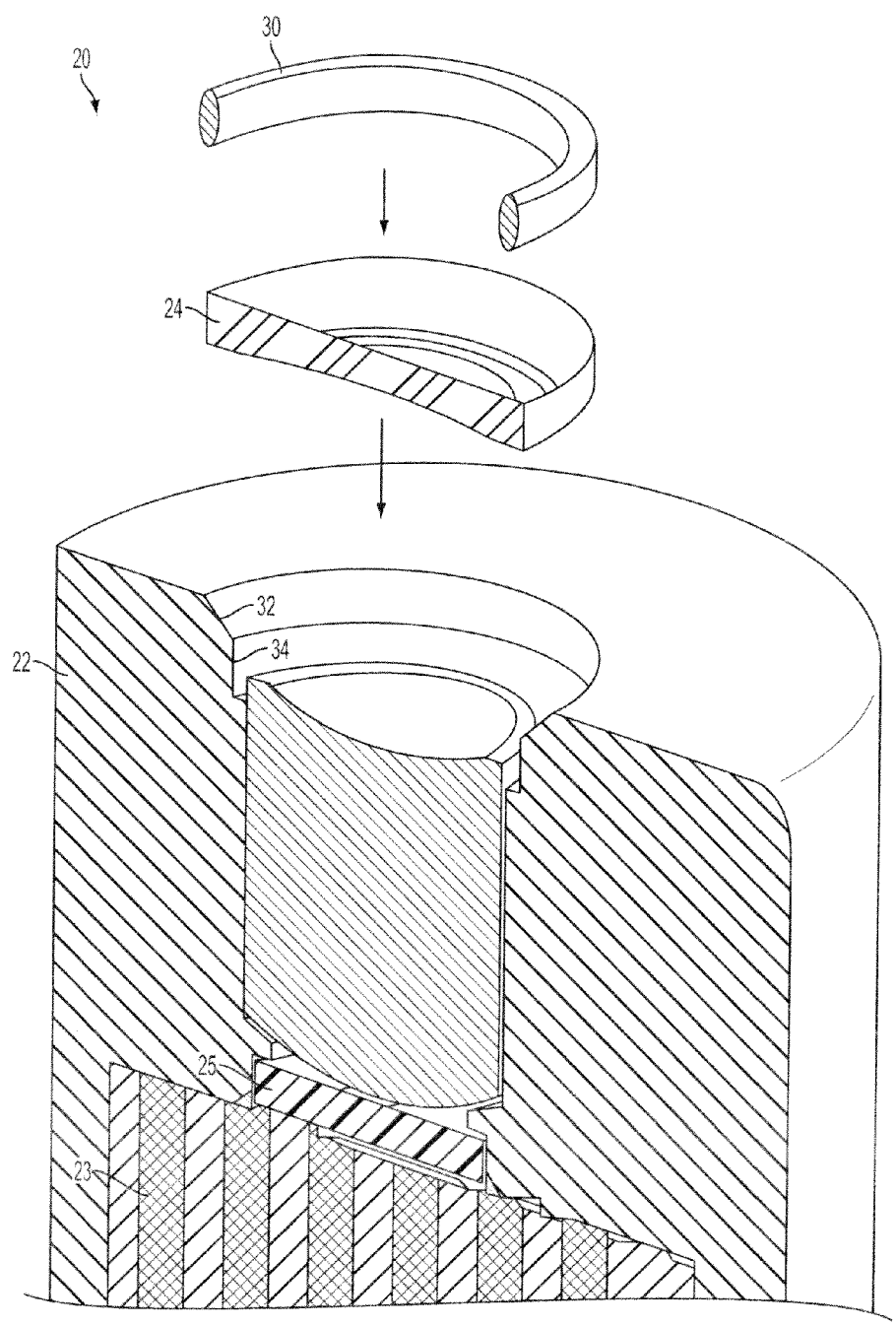
FIG. 3 is a partially exploded sectional view of the camera assembly similar to FIG. 2, with a sealing member and optical element being separated from an optical housing.

Turning now to FIG. 3, a method of forming the optical system 10, and specifically the camera assembly 20 thereof, will now be described. FIG. 3 depicts a partially exploded sectional view of the camera assembly 20. In this example, the optical housing 22, optical element 24, and sealing member 30 are again shown in sectional form in an effort to more clearly depict the relative locations of the optical element 24 and sealing member 30 with respect to the optical housing 22. Further, it is to be appreciated that the camera assembly 20 is shown in exploded form for illustrative purposes to show the structural relationship between the optical housing 22, optical element 24, and sealing member 30. In operation, however, the camera assembly 20 will be in a fully assembled state in a manner similar to that shown in FIG. 1.

As shown in FIG. 3, the optical element 24 is positionable within the optical housing 22. In this example, the optical element 24 will be positioned within an opening 34 formed in the optical housing 22. While only a sectional view of the opening 34 is shown in this example, the opening 34 can have a generally circular shape in operation. In other examples, however, the opening 34 includes any number of shapes (e.g., oval shapes, quadrilateral shapes, etc.) to accommodate for varying sizes/shapes of the optical element 24. In still further examples, the optical housing 22 is not limited to including the opening 34, and instead, the optical element 24 could be sealed to the optical housing 22 without the opening 34.

With the optical element 24 positioned within the opening 34, the sealing member 30 will then be used to seal the optical element 24 with respect to the optical housing 22. It is to understood that the sealing member 30 is shown in an annular form to shown the fitting that occurs between the optical housing and the optical element 24. Of course, it is to be appreciated that the initial frit may have a particulate/powdered form, possibly as part of a paste.

It is to be understood that the sealing member 30 can be applied either before or after the optical element 24 engages the optical housing 22 (i.e., is positioned within the opening 34). For instance, in one possible example, the sealing member 30 (i.e., initial frit, such as in paste-form) is applied to one of the optical element 24 or optical housing 22 before the optical element 24 engages the optical housing 22. In another example, the sealing member 30 (i.e., the initial frit) is applied after the optical element 24 engages the optical housing 22.

The sealing member 30 is somewhat generically schematically depicted in FIG. 3. In this example, the sealing member 30 includes a generally oval-shaped to its cross-sections. Of course, since the sealing member 30 may initially be in a particulate/powder form, the sealing member 30 is not limited to such a shape. Rather, the sealing member 30 may include a wide variety of sizes and shapes, depending on the specific application. The sealing member 30 is disposed between the optical housing 22 and optical element 24. In this example, the sealing member 30 will be positioned in (e.g., within) or near the groove 32. The sealing member 30 will therefore be in initial contact with each of the optical housing 22 and optical element 24.

Figure 4:
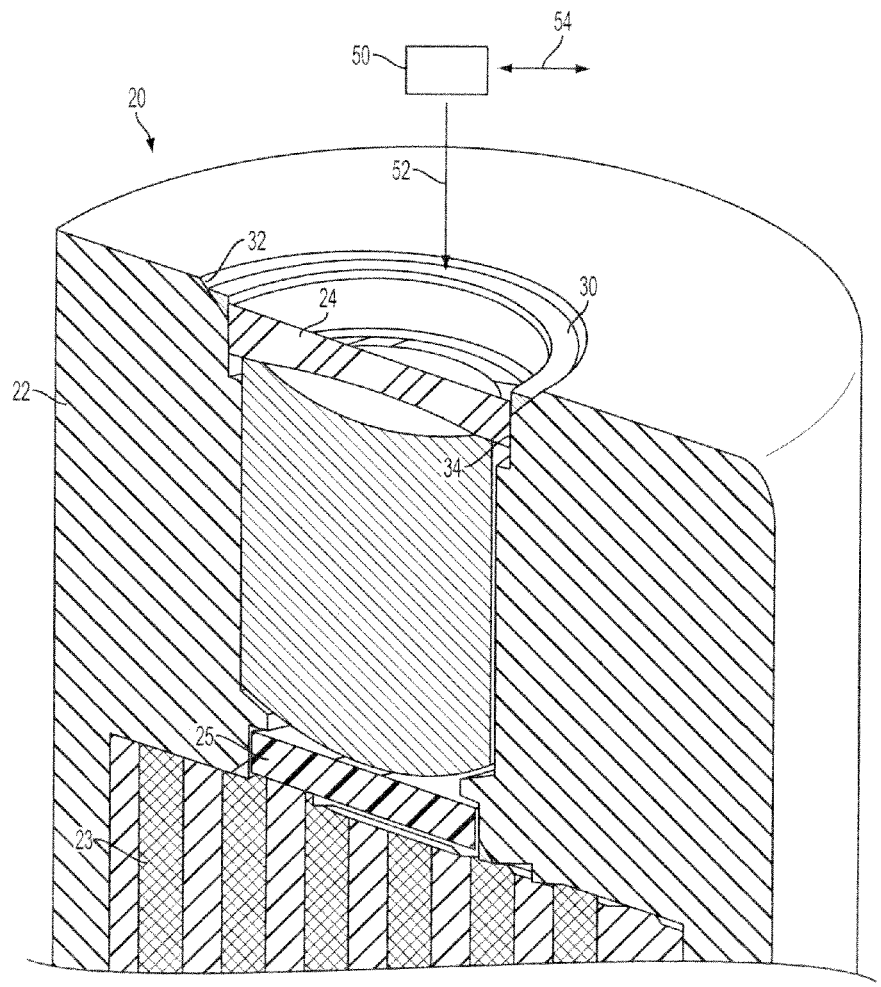
FIG. 4 is a sectional view of the camera assembly similar to FIG. 2, with a heating source heating the sealing member.

Turning now to FIG. 4, with the optical element 24 and sealing member 30 in place, a heating source 50 will seal the sealing member 30 with respect to the optical housing 22 and optical element 24. It is to be appreciated that the heating source 50 is generically/schematically shown in FIG. 4 for ease of illustration. Indeed, the heating source 50 includes any number of heating sources, some of which may be known. For example, the heating source 50 includes infrared heating or light sources, laser heating sources, bulbs, high intensity bulbs, etc.

The heating source 50 provides heat 52 (shown schematically with arrowhead) to the sealing member 30 to at least partially melt the sealing member 30. The heating source 50 provides localized heating to the sealing member 30 to control the flow of the sealing member 30 upon heating/melting. While the heating source 50 includes a wide range of beam sizes, in one possible example, the heating source 50 has an approximately 1 millimeter (approximately 0.04 inches) diameter spot size. Of course, other spot sizes are envisioned.

By at least partially melting, the sealing member 30 will flow into the groove 32 and substantially surround the optical element 24. In particular, the sealing member 30 will surround an outer edge of the optical element 24 while simultaneously contacting the optical housing 22 (i.e., contacting walls of the groove 32). This flow of the sealing member 30 is controlled due to the localized heating by the heating source 50. As such, flow of the sealing member 30 to unintended areas of the optical housing 22 (e.g., in a direction away from the optical element 24) is reduced/limited. In a further example, the heating source 50 may not only heat the sealing member 30, but may also heat portions of the optical housing 22 that are adjacent the sealing member 30. In such an example, these portions of the optical housing 22 will heat up, thus heating the sealing member 30 and causing the sealing member 30 to melt and flow.

The heating source 50 and sealing member 30 will move relative to each other such that substantially all of the sealing member 30 will be heated. In the shown example, the heating source 50 can move along a direction 54 (shown generically/schematically with arrowhead). This direction 54 can substantially match the shape of the sealing member 30. For instance, when the sealing member 30 extends annularly along the optical housing 22, the direction 54 along which the heating source 50 moves can generally match this annular shape. Of course, in other examples, the sealing member 30 is not limited to extending annularly, and the direction 54 of the heating source 50 can be adjusted accordingly (i.e., by extending along a straight line, by making one or more bends/curves, etc.). In this example, the optical housing 22 and sealing member 30 will remain relatively stationary with respect to the heating source 50.

In further examples, the heating source 50 is not limited to moving along the direction 54. Instead, the heating source 50 may be relatively stationary, while the optical housing 22 and sealing member 30 move along the direction 54. In such an example, the optical housing 22 and sealing member 30 can rotate, such that the heating source 50 applies the heat 52 while remaining relatively stationary.

In either of these examples, it is to be understood that the relative speeds of the heating source 50 and/or the optical housing 22 are adjustable depending on the desired characteristics of the seal formed by the sealing member 30. For example, characteristics that may affect the relative speeds of the heating source 50 and/or the optical housing 22 include the intensity of the heat 52, material of the sealing member 30, amount/thickness of the sealing member 30, air temperature/humidity, etc. As such, the relative speeds of the heating source 50 and/or optical housing 22 may be at least fast enough to melt the sealing member 30 and effectively seal the optical housing 22 and optical element 24.

Of course, if other heating arrangements (e.g., simultaneous annular heating) are contemplated. If such other heating arrangements are utilized, appropriate heat application and control are provided.

Figure 5:
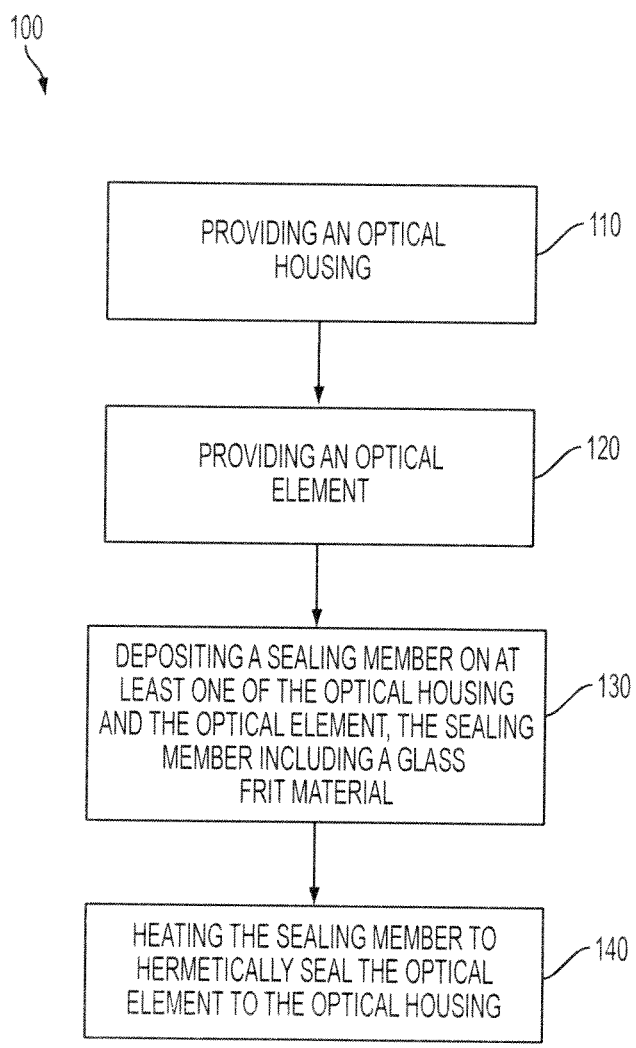
FIG. 5 is a flowchart depicting a method of forming the optical system.

Turning now to FIG. 5, an example method 100 of forming the optical system 10 is shown. The method 100 can be performed in association with the example optical system 10 and camera assembly 20 shown and described above with reference to FIGS. 1 to 4.

The method 100 includes a step 110 of providing the optical housing 22. In particular, as described with respect FIGS. 1 to 4, the optical housing 22 is disposed at the end of the probe assembly 18. The optical housing 22 will house and protect optical structures (e.g., wires, lenses, fiber optic bundles, etc.) from moisture, humidity, and/or other environmental conditions.

The method 100 further includes a step 120 of providing the optical element 24. In particular, as described above with respect to FIGS. 1 to 4, the optical element 24 includes one or more lenses, apertures, or the like, that assist in the acquiring of images/video. The optical element 24 can focus light from the area onto fiber optic bundles, or the like, that are housed within the optical housing 22.

The method 100 further includes a step 130 of depositing the sealing member 30 on at least one of the optical housing 22 and the optical element 24, wherein the sealing member 30 includes the glass frit material. In particular, as described with respect to FIG. 3, the sealing member 30 can initially be in a particulate/powder form and includes glass frit material. The sealing member 30 will be positioned between the optical housing 22 and optical element 24 within the groove 32. As such, the sealing member 30 is in initial contact with each of the optical housing 22 and optical element 24.

The method 100 further includes a step 140 of heating the sealing member 30 to hermetically seal the optical element 24 to the optical housing 22. In particular, as described with respect to FIG. 4, the heating source 50 will provide heat 52 to the sealing member 30. The heating source 50 (or the optical housing 22) will move along the direction 54 such that the heating source 50 heats substantially all of the sealing member 30. This heating will cause the sealing member 30 to melt, thus forming the hermetic seal between the optical element 24 and the optical housing 22. Accordingly, air, water, moisture, condensation, etc. will be limited/restricted from passing through the sealing member 30 and into the optical housing 22.

Providing the sealing member 30 as including the glass frit material will produce a number of benefits. First, the sealing member 30 is generally airtight and resistant to the passage of water, moisture, condensation, etc. Further, as compared to previously used epoxies, the glass frit material is more resistant to chemical attacks and the resulting degradation of the seal due to these chemical attacks. Further still, the glass frit material forming the sealing member 30 will also remain effective despite relatively high temperature fluctuations to which the camera assembly 20 may be exposed.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. An optical system for inspecting an area, the optical system including:
    an optical housing having an interior configured to house one or more optical fibers;
    an optical element housed within the optical housing for focusing light onto the one or more optical fibers, the optical element having a outermost portion located at a junction of the interior of the optical housing to an exterior; and
    a sealing member located at the junction of the interior of the optical housing to the exterior and configured to seal the optical element with respect to the optical housing at the outermost portion of the optical element and seal the interior of the optical housing from the exterior, the sealing member including a solidified heat-solidified glass frit material.

2. The optical system of claim 1, wherein the optical housing includes a boroscope probe tip.

3. The optical system of claim 2, wherein the optical element includes a lens for sealing to the boroscope probe tip.

4. The optical system of claim 1, wherein the optical housing is included as part of a boroscope assembly.

5. The optical system of claim 1, wherein the sealing member further includes a binder material for binding to the glass frit material.

6. The optical system of claim 1, wherein the sealing member is disposed between the optical housing and the optical element, the sealing member being in contact with each of the optical housing and the optical element.

7. The optical system of claim 6, wherein the sealing member is disposed annularly between the optical housing and the optical element.

8. The optical system of claim 1, wherein the sealing member is configured to be heated by a heating source to seal the optical element with respect to the optical housing.

9. The optical system of claim 8, wherein the sealing member includes a binder material.

10. An optical system for inspecting an area, the optical system including:
    an optical housing having an interior configured to house one or more optical fibers;
    an optical element housed within the optical housing for focusing light onto the one or more optical fibers, the optical element having a outermost portion located at a junction of the interior of the optical housing to an exterior; and
    a sealing member located at the junction of the interior of the optical housing to the exterior and disposed annularly between the optical housing and the outermost portion of the optical element to seal the optical element with respect to the optical housing at the outermost portion of the optical element and seal the interior of the optical housing from the exterior, the sealing member including a solidified heat-solidified glass frit material.

11. The optical system of claim 10, wherein the optical housing includes a boroscope probe tip.

12. The optical system of claim 11, wherein the optical element includes a lens for sealing to the boroscope probe tip the optical housing has an annular groove formed therein, the annular groove has a general shape that matches a shape of an outer edge of the lens and the sealing member is located within the annular groove and is located annularly about the lens.

13. The optical system of claim 10, wherein the optical housing is included as part of a boroscope assembly.

14. The optical system of claim 10, wherein the sealing member further includes a binder material for binding to the glass frit material.

15. The optical system of claim 10, wherein the sealing member is exposed to the exterior, and is configured to be directly heated by a heating source to seal the optical element with respect to the optical housing.

16. The optical system of claim 15, wherein the sealing member includes a binder material that is at least partially burned-off by the directly applied heat.

17. A method of forming an optical system, the method including the steps of:
   providing an optical housing having an interior configured to house one or more optical fibers;
   providing an optical element, the optical element having a outermost portion located at a junction of the interior of the optical housing to an exterior;
   depositing a sealing member at a location at the junction of the interior of the optical housing to the exterior, the sealing member including a glass frit material; and
   heating the sealing member to hermetically seal the optical element to the optical housing at the outermost portion of the optical element and seal the interior of the optical housing from the exterior.

18. The method of claim 17, wherein the step of heating the sealing member includes using a heating source to heat the sealing member and achieve at least a semifluid state so that frit particles within the glass frit material can flow together.

19. The method of claim 17, wherein the optical housing is provided as part of a boroscope assembly.

20. The method of claim 17, wherein the step of depositing the sealing member includes depositing the sealing member annularly on at least one of the optical housing and the optical element in an annular groove formed in the optical housing and which has a general shape that matches a shape of an outer edge of the optical element.

* * * * *